US012714345B2

(12) United States Patent
Tian et al.

(10) Patent No.: US 12,714,345 B2
(45) Date of Patent: Aug. 25, 2026

(54) SOFT STRETCHABLE COMPOSITES AND TECHNIQUES FOR THE FORMATION THEREOF

(71) Applicant: The Texas A&M University System, College Station, TX (US)

(72) Inventors: Limei Tian, College Station, TX (US); Myeong Namkoong, College Station, TX (US)

(73) Assignee: The Texas A&M University System, College Station, TX (US)

( * ) Notice: Subject to any disclaimer, the term of this patent is extended or adjusted under 35 U.S.C. 154(b) by 316 days.

(21) Appl. No.: 18/278,763

(22) PCT Filed: Feb. 25, 2022

(86) PCT No.: PCT/US2022/018015
§ 371 (c)(1),
(2) Date: Aug. 24, 2023

(87) PCT Pub. No.: WO2022/183061
PCT Pub. Date: Sep. 1, 2022

(65) Prior Publication Data

US 2024/0122516 A1 Apr. 18, 2024

Related U.S. Application Data

(60) Provisional application No. 63/154,703, filed on Feb. 27, 2021.

(51) Int. Cl.
*A61B 5/268* (2021.01)
*A61B 5/257* (2021.01)

(52) U.S. Cl.
CPC .............. *A61B 5/268* (2021.01); *A61B 5/257* (2021.01); *A61B 2562/0215* (2017.08); *A61B 2562/0285* (2013.01); *A61B 2562/125* (2013.01)

(58) Field of Classification Search
CPC ........... A61B 5/125; A61B 5/25; A61B 5/268; A61B 2562/125
See application file for complete search history.

(56) References Cited

U.S. PATENT DOCUMENTS

2020/0401042 A1 12/2020 Bao et al.
2021/0244304 A1 * 8/2021 Park .................. H01B 13/0036

FOREIGN PATENT DOCUMENTS

EP 3276693 A1 1/2018

OTHER PUBLICATIONS

Kim et al. Highly Conductive Pedot:PSS Nanofibrils Induced by Solution-Processed Crystallization. 2014.26,2268-2272. (Year: 2014).*

(Continued)

*Primary Examiner* — Eun Hwa Kim
(74) *Attorney, Agent, or Firm* — Jackson Walker LLP

(57) ABSTRACT

In an embodiment, the present disclosure pertains to an electrode having a first layer and a second layer. In some embodiments, the first layer includes a conductive polymer. In some embodiments, the second layer is positioned above the first layer. In some embodiments, the second layer includes an inorganic material that forms a conductive network on the first layer. In an additional embodiment, the present disclosure pertains to a method of making an electrode. In general, the method providing a mold with a desired indented pattern, pouring a solution including a conductive polymer into the indented pattern to form a first layer, and pouring a solution including an inorganic material onto the first layer to form a second layer. In some embodiments, the inorganic material forms a conductive network on the first layer.

11 Claims, 12 Drawing Sheets

(56) References Cited

OTHER PUBLICATIONS

Liu, Y. et al.; "Ultrasmooth, highly conductive and transparent PEDOT:PSS/silver nanowire composite electrode for flexible organic light-emitting devices"; Organic Electronics, vol. 31, Feb. 5, 2016; pp. 247-252.

Fang, Y. et al.; "Solution-Processed Submicron Free-Standing, Conformal, Transparent, Breathable Epidermal Electrodes"; ACS Appl. Mater. Interfaces. Journal, May 4, 2020; pp. 23689-23696.

* cited by examiner

FIG. 6A
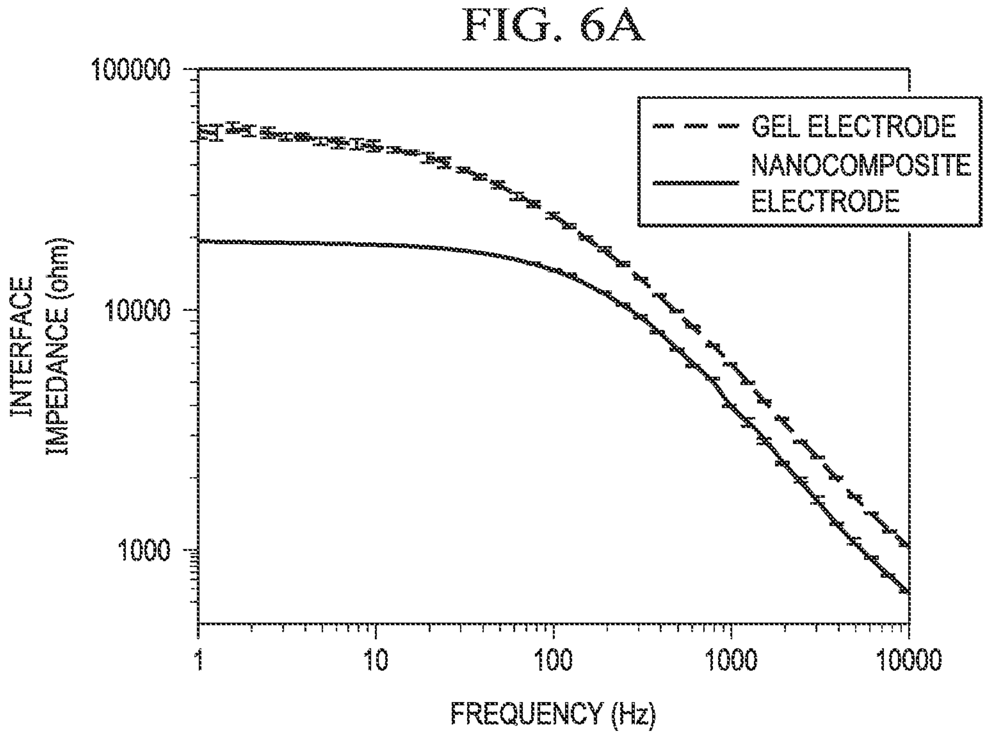
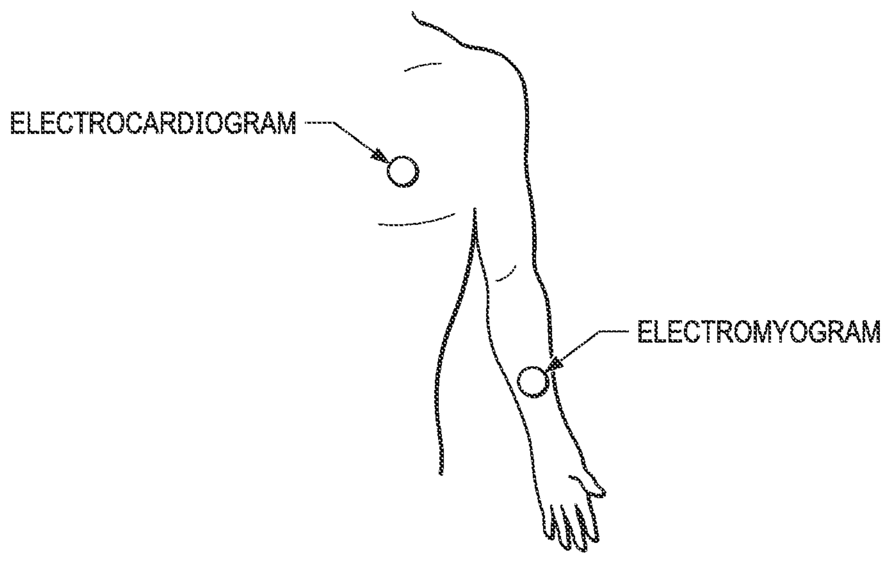
FIG. 6B

SOFT STRETCHABLE COMPOSITES AND TECHNIQUES FOR THE FORMATION THEREOF

CROSS-REFERENCE TO RELATED APPLICATIONS

This patent application claims priority from, and incorporates by reference the entire disclosure of, U.S. Provisional Application 63/154,703 filed on Feb. 27, 2021.

STATEMENT REGARDING FEDERALLY SPONSORED RESEARCH

This invention was made with government support under 1648451 awarded by the National Science Foundation. The government has certain rights in the invention.

TECHNICAL FIELD

The present disclosure relates generally to stretchable composites and more particularly, but not by way of limitation, to soft stretchable composites and techniques for the formation thereof.

BACKGROUND

This section provides background information to facilitate a better understanding of the various aspects of the disclosure. It should be understood that the statements in this section of this document are to be read in this light, and not as admissions of prior art.

Skin-inspired soft and stretchable electronic devices based on functional nanomaterials have broad applications such as health monitoring, human-machine interface, and the Internet of things. Solution-processed conductive nanocomposites have shown great promise as a building block of soft and stretchable electronic devices. However, realizing conductive nanocomposites with high conductivity, electromechanical stability, and low modulus over a large area at sub-100 μm resolution remains challenging.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure pertains to an electrode having a first layer and a second layer. In some embodiments, the first layer includes a conductive polymer. In some embodiments, the second layer is positioned above the first layer. In some embodiments, the second layer includes an inorganic material that forms a conductive network on the first layer.

In an additional embodiment, the present disclosure pertains to a method of making an electrode. In general, the method providing a mold with a desired indented pattern, pouring a solution including a conductive polymer into the indented pattern to form a first layer, and pouring a solution including an inorganic material onto the first layer to form a second layer. In some embodiments, the inorganic material forms a conductive network on the first layer.

In a further embodiment, the present disclosure pertains to a method of detecting an electrical signal from a surface. In general, the method includes placing an electrode on the surface and detecting the electrical signal from the surface. In some embodiments, the electrode includes a first layer and a second layer. In some embodiments, the first layer includes a conductive polymer. In some embodiments, the second layer is positioned above the first layer. In some embodiments, the second layer includes an inorganic material that forms a conductive network on the first layer.

In another embodiment, the present disclosure pertains to a method of transmitting an electrical signal to a surface. In general, the method includes placing an electrode on the surface and transmitting the electrical signal to the surface. In some embodiments, the electrode includes a first layer and a second layer. In some embodiments, the first layer includes a conductive polymer. In some embodiments, the second layer is positioned above the first layer. In some embodiments, the second layer includes an inorganic material that forms a conductive network on the first layer.

In an embodiment, the present disclosure pertains to an electrode having a layer that includes at least one of a conductive polymer or an inorganic material.

In a further embodiment, the present disclosure pertains to a method of making an electrode. In general, the method includes providing a mold with a desired indented pattern and pouring a solution having at least one of a conductive polymer or an inorganic material onto the mold to form a layer.

In an additional embodiment, the present disclosure pertains to a method of detecting an electrical signal from a surface. In general, the method includes placing an electrode on the surface and detecting the electrical signal from the surface. In some embodiments, the electrode includes a layer having at least one of a conductive polymer or an inorganic material.

In another embodiment, the present disclosure pertains to a method of transmitting an electrical signal to a surface. In general, the method includes placing an electrode on the surface and transmitting the electrical signal to the surface. In some embodiments, the electrode includes a layer having at least one of a conductive polymer or an inorganic material.

BRIEF DESCRIPTION OF THE DRAWINGS

A more complete understanding of the subject matter of the present disclosure may be obtained by reference to the following Detailed Description when taken in conjunction with the accompanying Drawings wherein:

FIG. 1A shows conductive nanocomposite components. FIG. 1B shows a cross-section structure of the nanocomposite. FIG. 1C shows a fabrication process according to aspects of the present disclosure.

FIG. 4A shows tensile stress-strain curves and FIG. 4B shows stress relaxation curves of PEDOT:PSS films prepared with 3 wt % TRITON™ X and varying concentrations of D-sorbitol from 0 wt % to 3 wt %. FIG. 4C shows elastic moduli comparison of the PEDOT:PSS films calculated from FIG. 4A and FIG. 4B. FIGS.

Figure 4A:
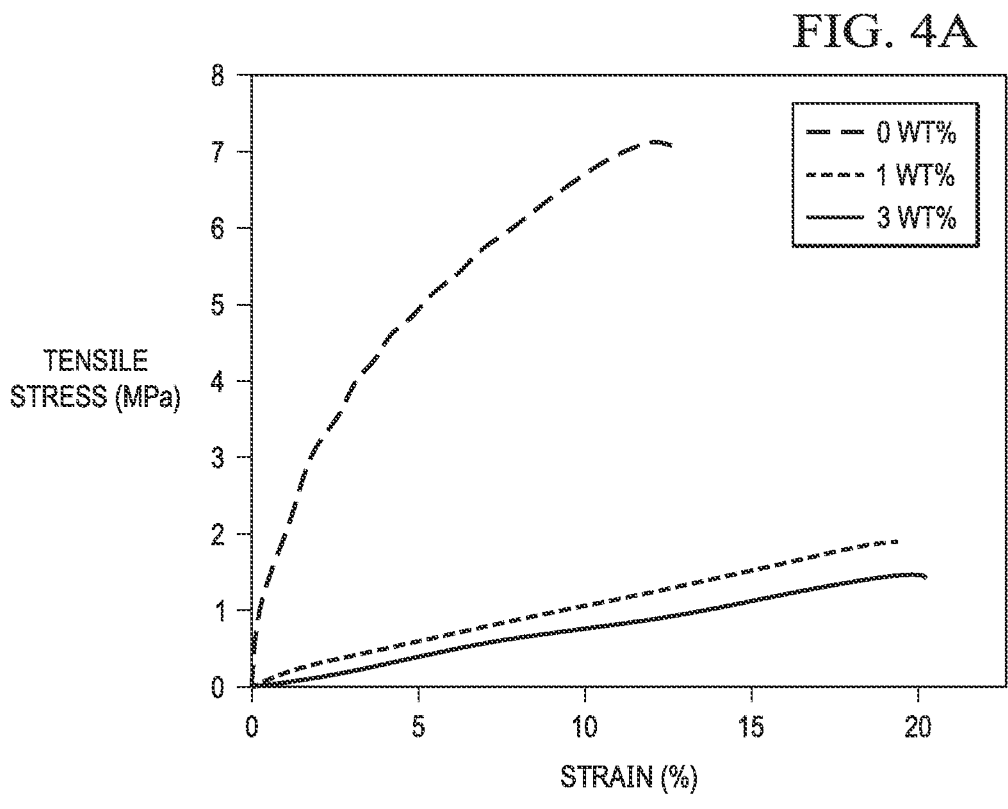
FIGS. 4A-4F illustrate electromechanical characterization of nanocomposite thin films.
Figure 4B:
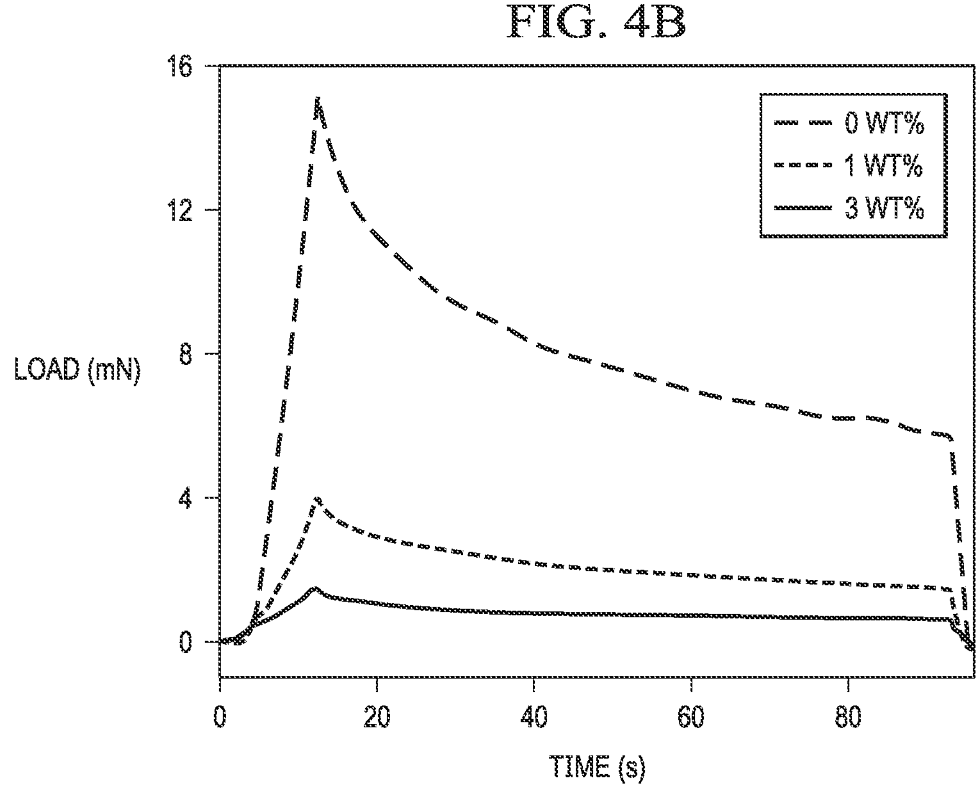
Figure 4C:
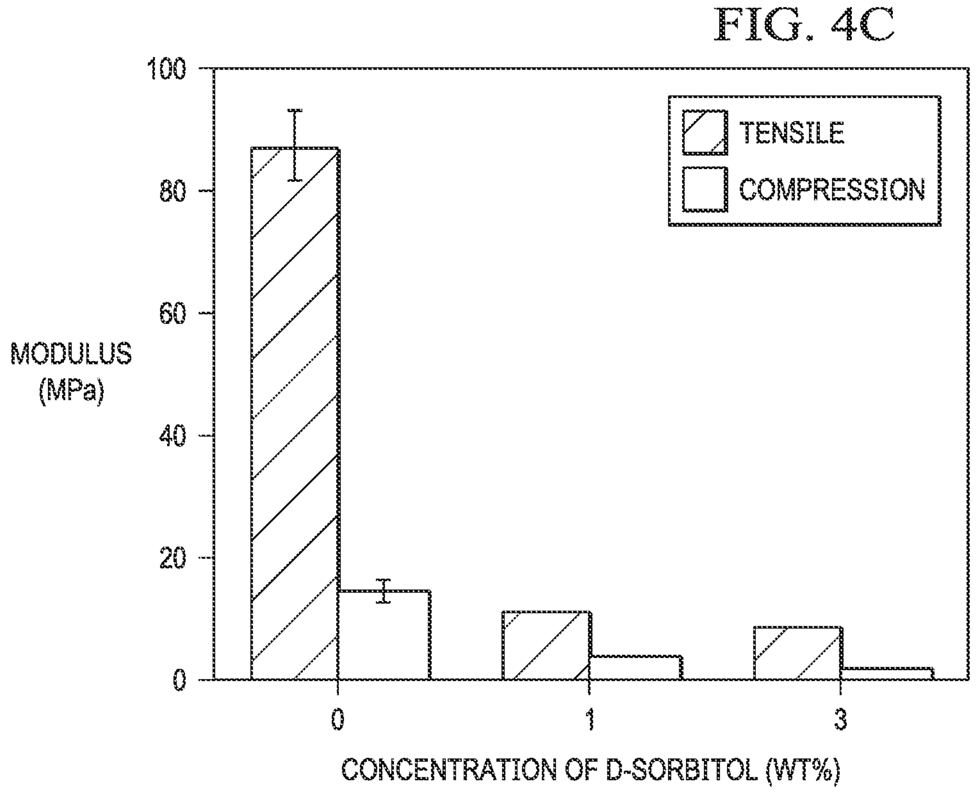
Figure 4D:
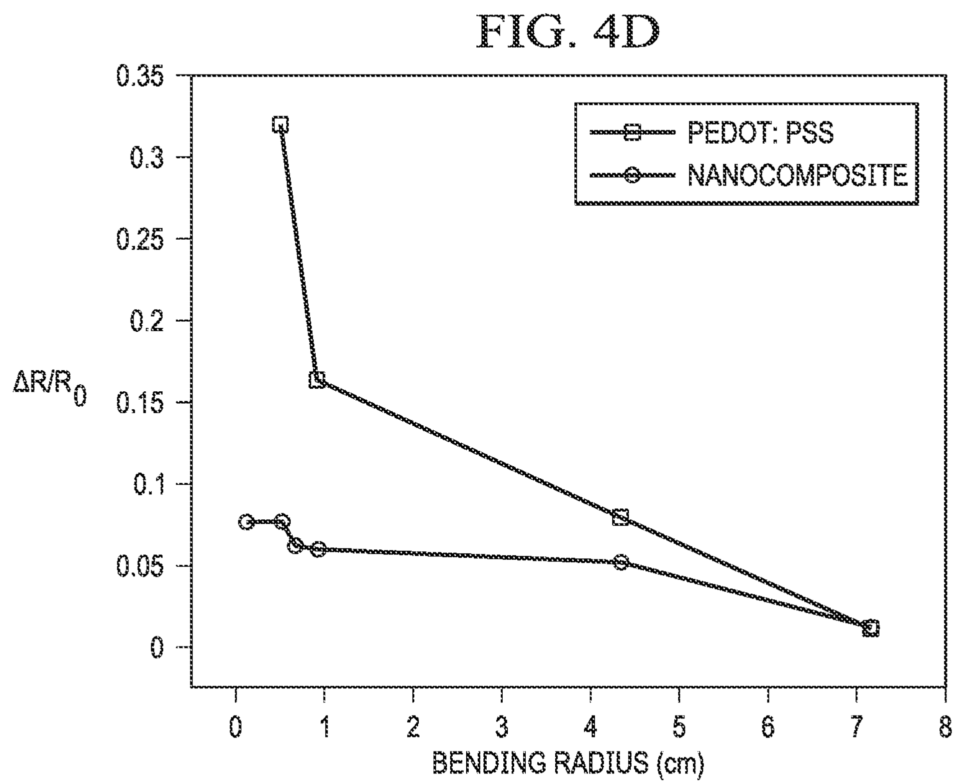
Figure 4E:
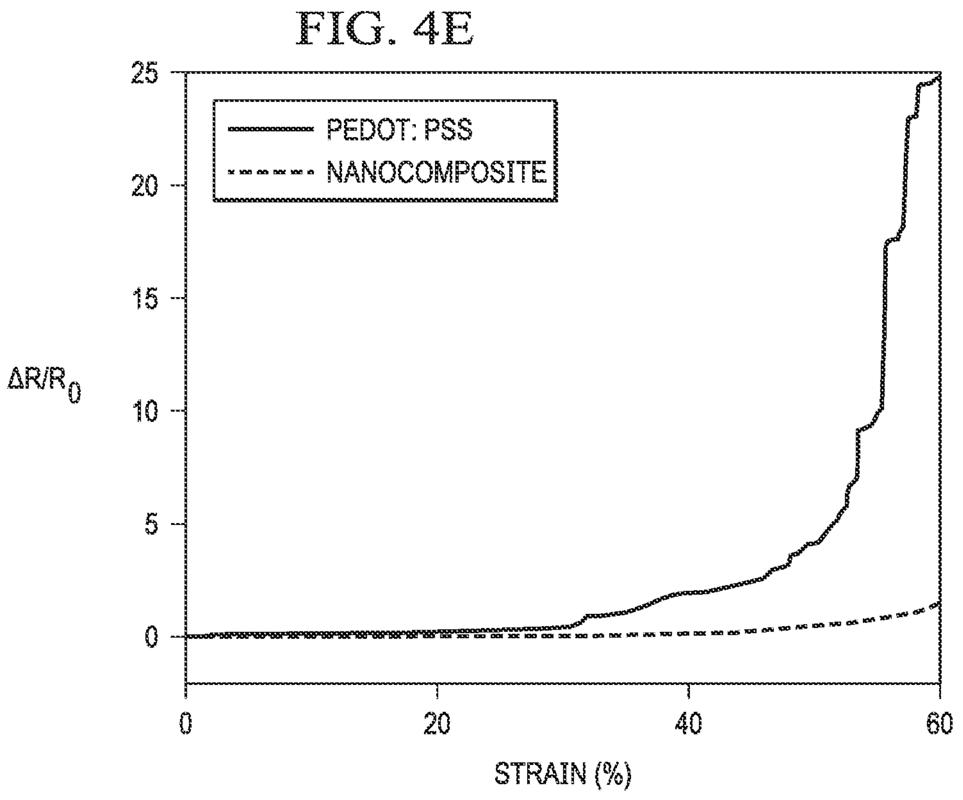
Figure 4F:
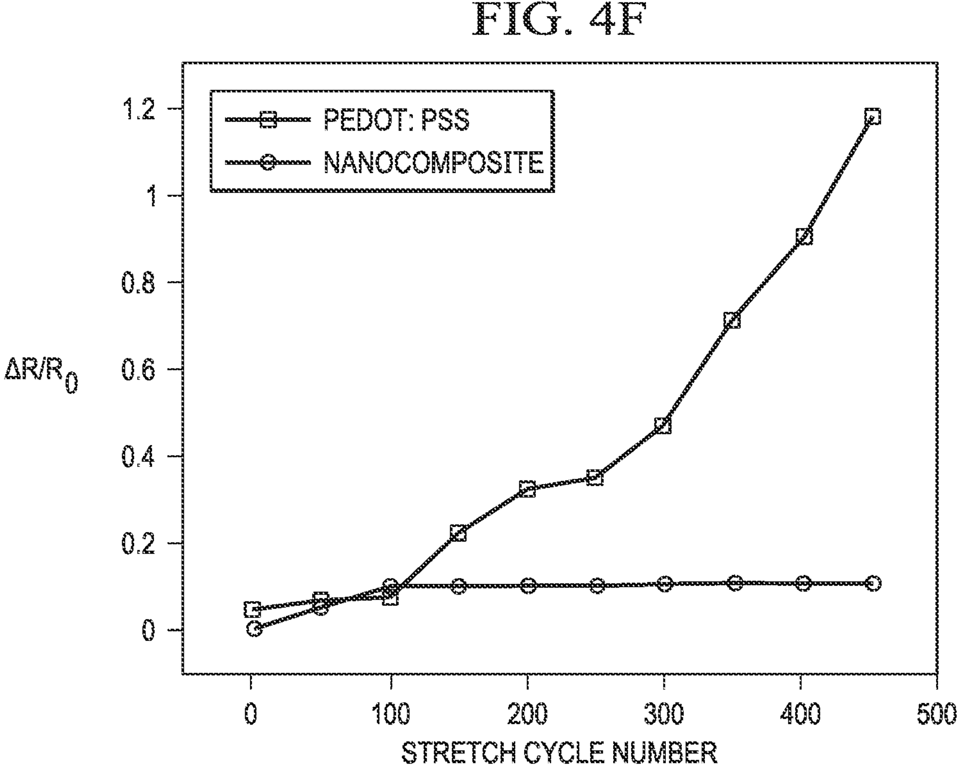

4D-4F shows resistance changes in the serpentine nanocomposite and PEDOT:PSS thin films under bending (FIG. 4D), under stretching (FIG. 4E), and after numerous stretch and release cycles (FIG. 4F).

Figure 5A:
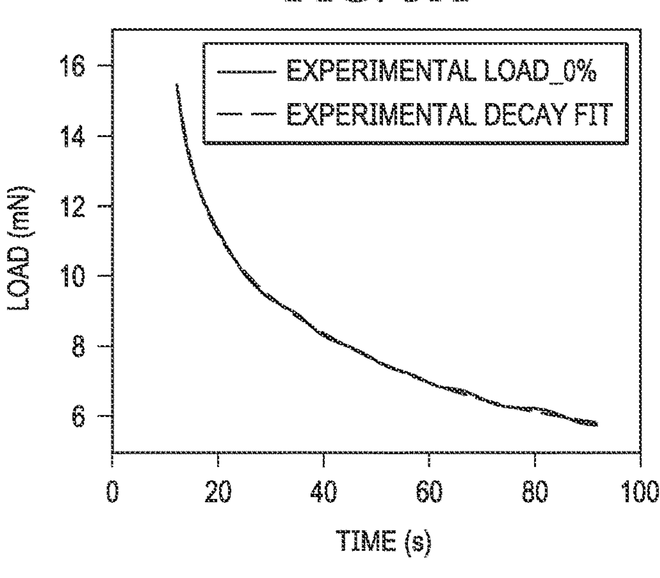
Figure 5B:
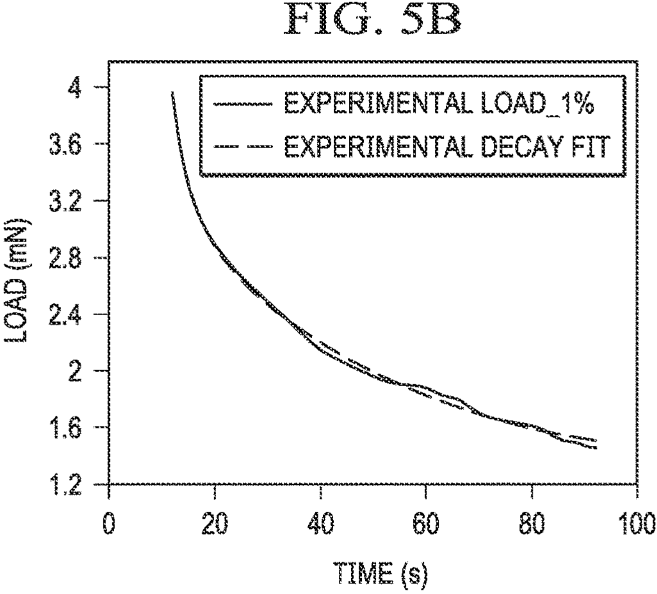
Figure 5C:
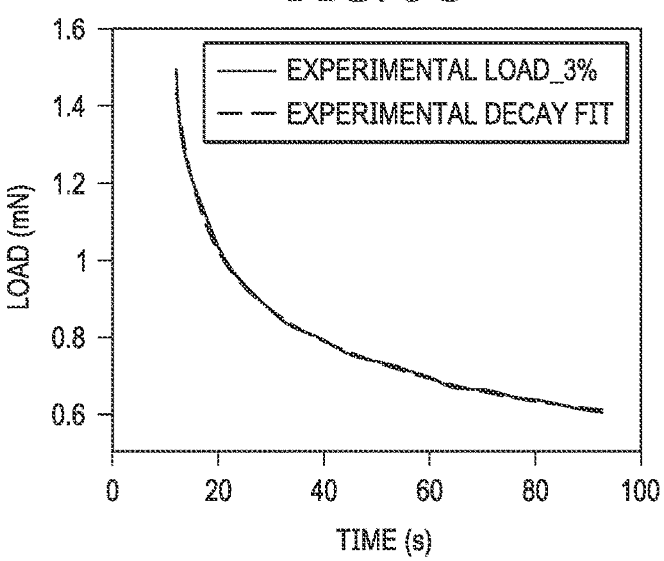

FIGS. 5A-5C illustrate the load versus time curves of the hold period fitted with a two-exponential decay equation for the PEDOT:PSS films prepared with D-sorbitol of 0 wt % (FIG. 5A), 1 wt % (FIG. 5B), and 3 wt % (FIG. 5C). The decay equation is $P=\gamma_0+A_1e^{-t/T1}+A_2e^{-t/T2}$ where P is the load, t is the time, and $\gamma_o$ is the load at equilibrium.

Figure 6C:
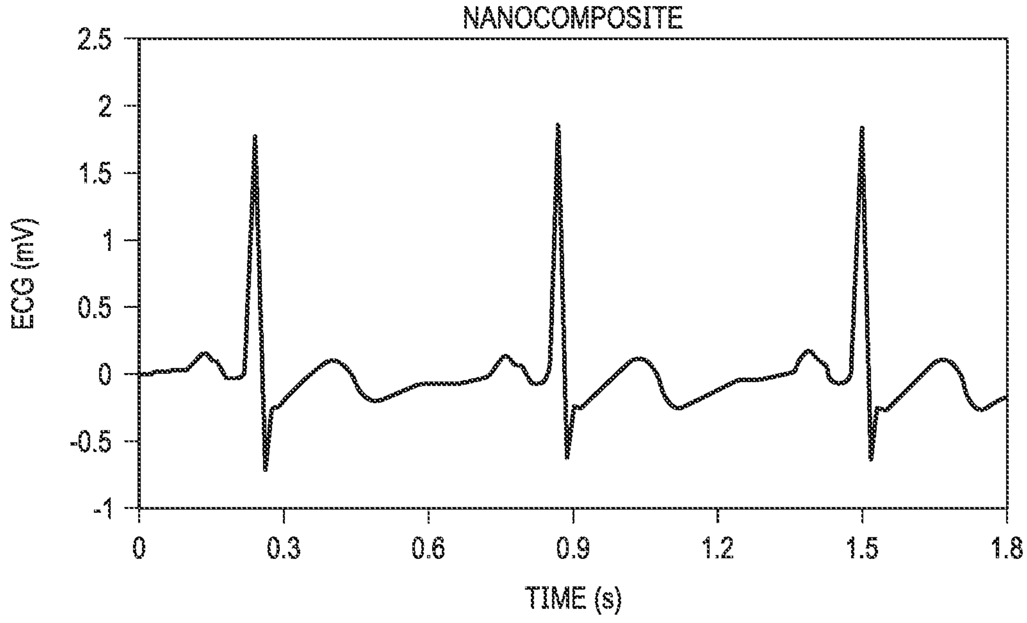
Figure 6C:
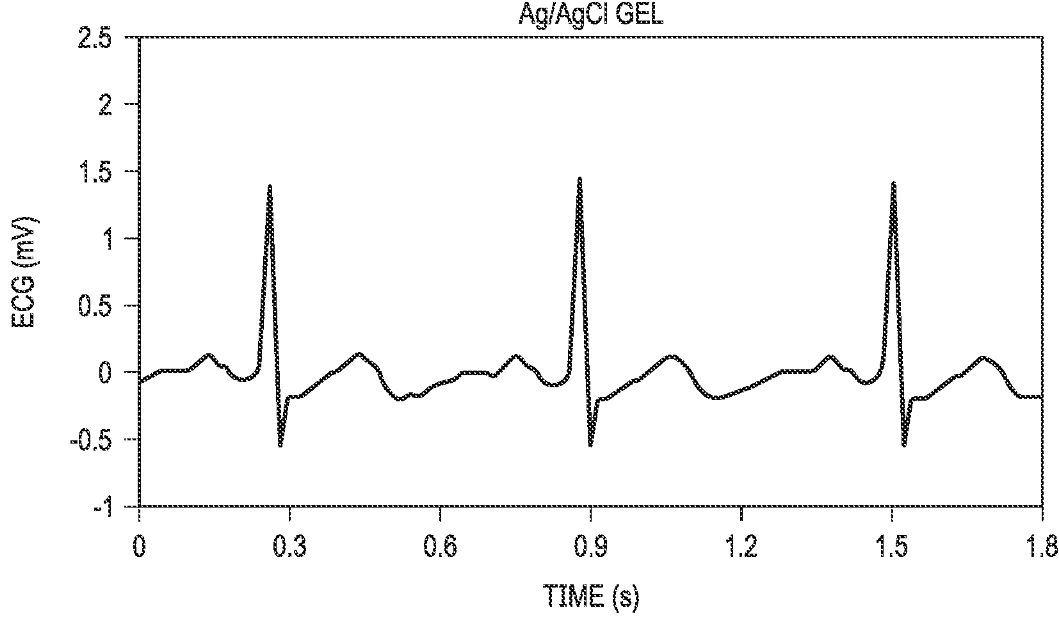
Figure 6D:
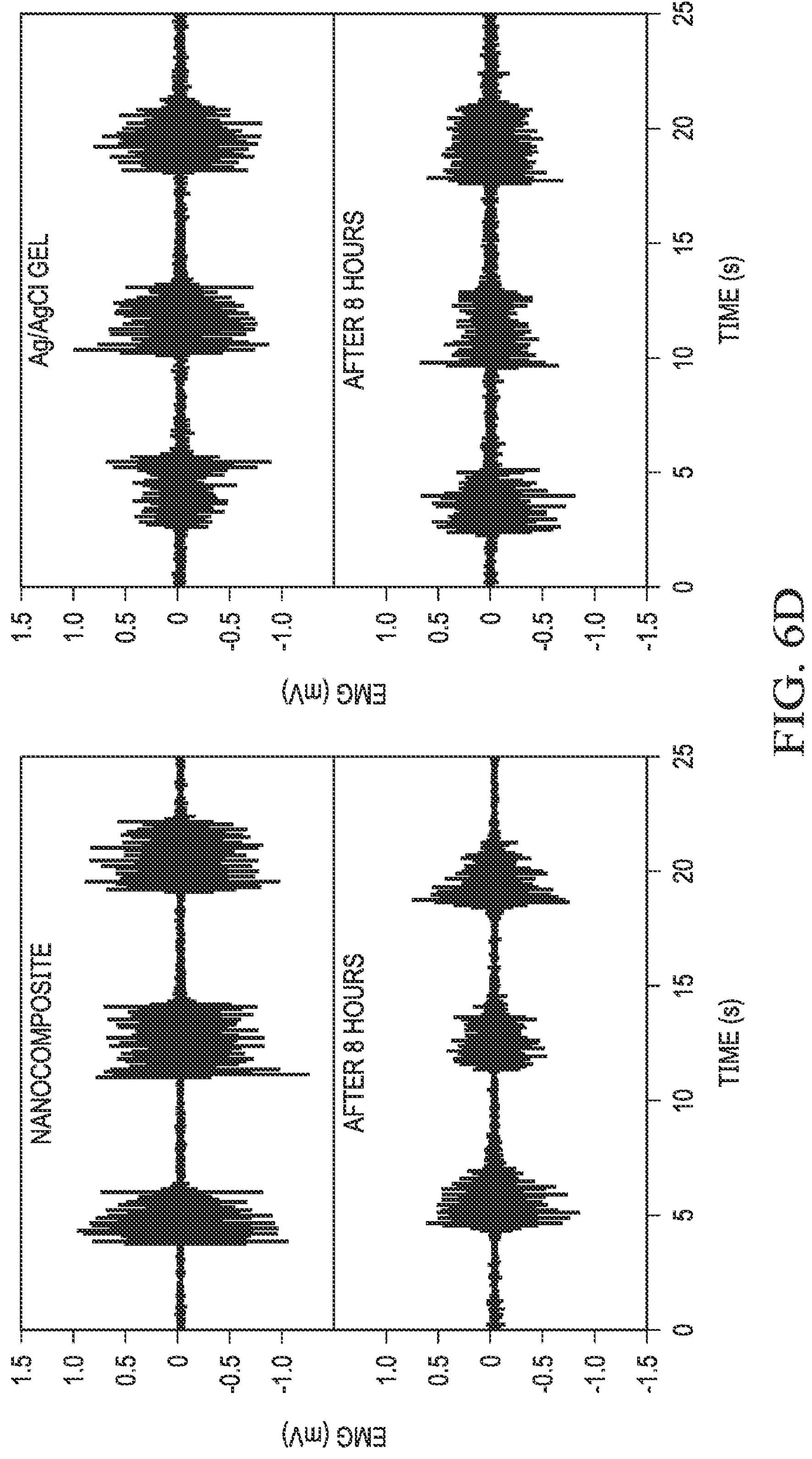

FIGS. 6A-6D illustrate electrocardiogram (ECG) and electromyogram (EMG) recordings. FIG. 6A shows a comparison of the skin-electrode interface electrical impedance measured with conventional Ag/AgCl gel electrodes and nanocomposite electrodes. FIG. 6B shows a schematic illustration of sensor locations for ECG and EMG recordings. FIG. 6C shows ECG signals measured with nanocomposite and gel electrodes. FIG. 6D shows EMG signals measured with nanocomposite mesh and gel electrodes before and after wearing for 8 hours.

Figure 7A:
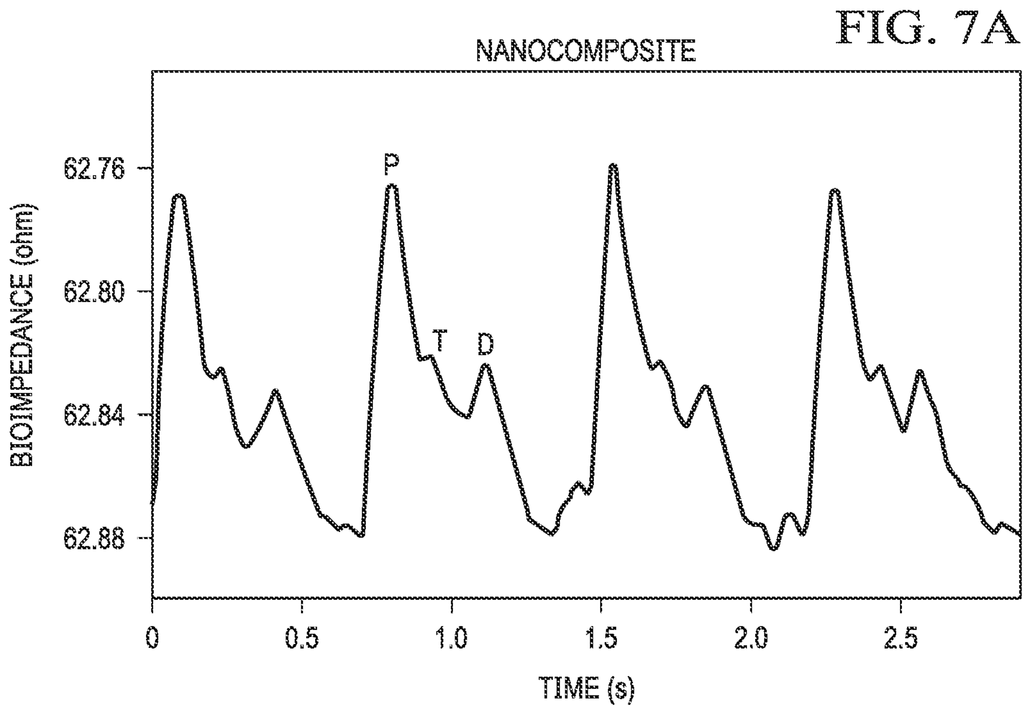
Figure 7B:
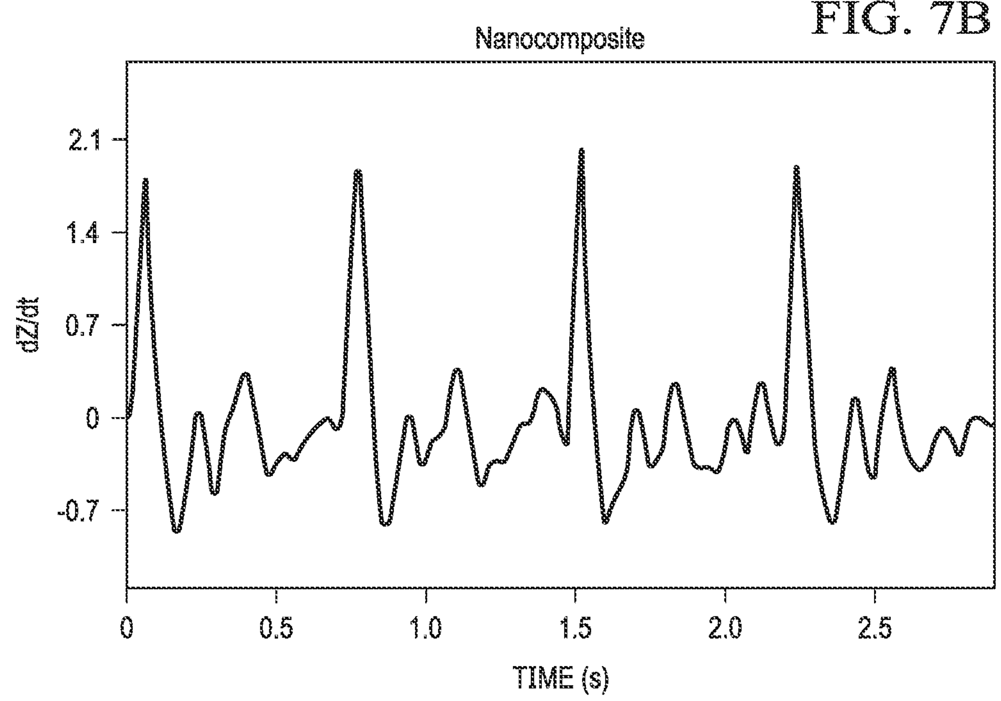
Figure 7C:
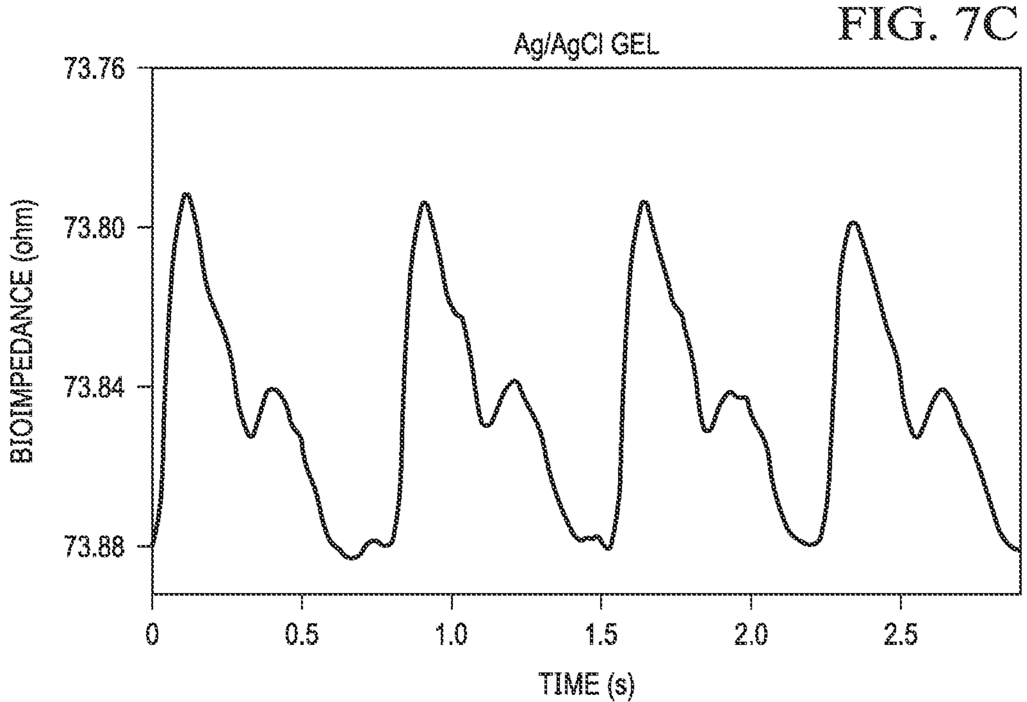
Figure 7D:
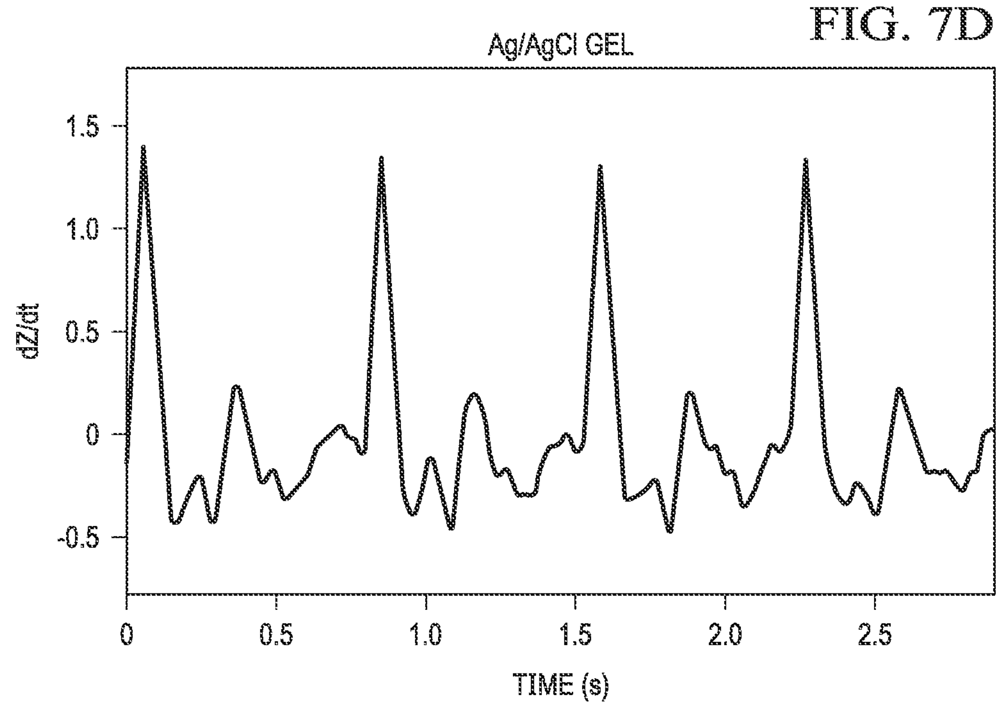

FIGS. 7A-7D illustrate bioimpedance measurements. FIG. 7A shows bioimpedance signals and FIG. 7B shows the first derivative with respect to time measured with nanocomposite electrodes. FIG. 7C shows bioimpedance signals and FIG. 7D shows the first derivative measured with gel electrodes.

DETAILED DESCRIPTION

It is to be understood that the following disclosure provides many different embodiments, or examples, for implementing different features of various embodiments.

Specific examples of components and arrangements are described below to simplify the disclosure. These are, of course, merely examples and are not intended to be limiting. The section headings used herein are for organizational purposes and are not to be construed as limiting the subject matter described.

In various aspects, the present disclosure pertains to a moldable, transferrable, high-performance conductive nanocomposite composed of an interpenetrating network of silver nanowires and poly(3,4-ethylenedioxythiophene):poly(styrenesulfonate). The stacked structure of the nanocomposite synergistically integrates the complementary electrical and mechanical properties of the individual components. The nanocomposite was patterned via a simple, low-cost micromolding process and then transferred the patterned large-area electrodes onto various substrates to realize soft, skin-interfaced electrophysiological sensors. Electrophysiological signals measured using the nanocomposite electrodes exhibit a higher signal-to-noise ratio than standard gel electrodes. The nanocomposite design and fabrication approach presented herein can be broadly employed for soft and stretchable electronic devices.

Recent advances in bioelectronics have led to a broad class of soft, ultrathin, stretchable wearables to measure various biophysical and biochemical signals associated with health and disease. Soft, high-performance wearable electronic devices require materials with high conductivity, electromechanical stability, and low modulus comparable to the human skin. Conductive and stretchable composites based on inorganic/organic nanomaterials, such as metal nanoparticles, nanowires, nanoribbons, nanofibrils, and nanomeshes, have been developed to overcome the limitation of conventional conductive materials and interfaces for high-quality physiological measurements and user comfort. Among many engineered materials, solution-processed conductive nanocomposites have shown great promise for realizing soft, ultrathin, and stretchable electronic devices owing to their tunable electrical and mechanical properties. However, conductive nanocomposites with homogeneously dispersed nanofillers in a non-conductive elastomeric matrix invariably exhibit a trade-off between high conductivity (requiring high volume fraction of the nanofiller) and high stretchability (requiring low volume fraction of the nanofiller). Overcoming this fundamental trade-off through novel material design and processing methods is useful to advance the solution-processable, high-performance wearable devices.

In addition, simple, scalable, and efficient processing methods to pattern functional materials are useful for realizing high-performance, high-density wearable electronics. For example, large-area, epidermal electronic devices fabricated in cleanroom facilities can measure multichannel, high-resolution, electrophysiological signals over the whole scalp, chest, and forearm. Various fabrication strategies have been developed to achieve skin-like wearables, including vacuum deposition, lithography, etching, and transfer printing, "cut-and-paste" method, laser patterning, screen printing, inject printing, and direct drawing on skin. However, a simple, low-cost, scalable fabrication approach for solution-processed nanomaterials over a large area at sub-100 μm resolution remains challenging.

In various aspects, the present disclosure introduces a moldable and transferrable conductive nanocomposite thin-film composed of an interpenetrating network of silver nanowires (AgNWs) and poly(3,4-ethylenedioxythiophene):poly(styrenesulfonate) (PEDOT:PSS). The stacked structure of the nanocomposites synergistically integrates the properties of highly conductive metal nanowires and intrinsically soft conductive polymers. A simple micromolding method is used to pattern the nanocomposite thin films with a feature dimension less than 25 μm. The patterned nanocomposite can be easily transferred onto various flexible and stretchable substrates to achieve wearable electronics with high breathability. These nanocomposites exhibit excellent electromechanical stability under bending and stretching, providing robust performance of wearable sensors. The electrophysiological recordings, including electrocardiogram (ECG), electromyogram (EMG), and electrical bioimpedance (EBI), show a higher signal-to-noise ratio compared to those collected with standard Ag/AgCl gel electrodes.

Reference will now be made to more specific embodiments of the present disclosure and data that provides support for such embodiments. However, it should be noted that the disclosure below is for illustrative purposes only and is not intended to limit the scope of the claimed subject matter in any way.

Figure 1A:
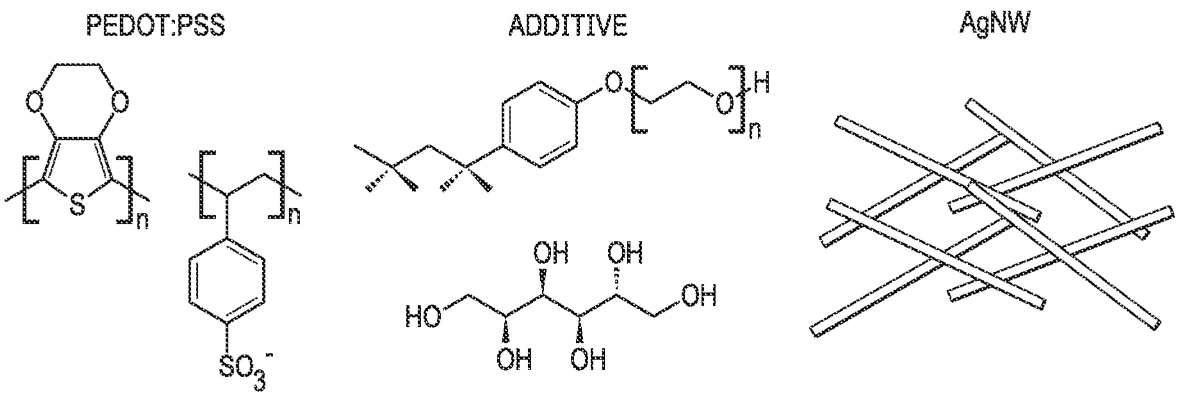
FIGS. 1A-1C illustrate a design of conductive nanocomposites.
Figure 1B:
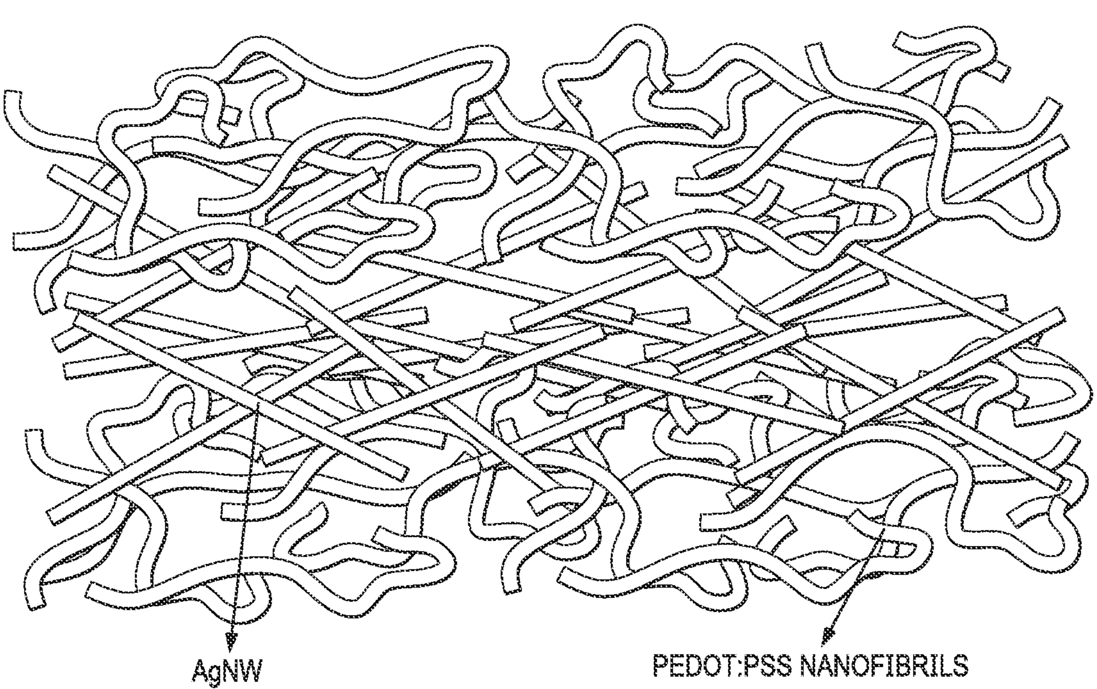

Design and patterning of conductive nanocomposites. In the nanocomposite design, two additives, TRITON™ X-100 and D-sorbitol, were employed to enhance the properties of the PEDOT:PSS films (FIG. 1A). Previously, these two additives were used separately to facilitate the formation of PEDOT:PSS nanofibrils, thereby enhancing the conductivity of the PEDOT:PSS films. Here, TRITON™ X improves the wetting properties of the PEDOT:PSS solution and enables the uniform coating of PEDOT:PSS on hydrophobic surfaces while D-sorbitol enhances the electrical conductivity, mechanical flexibility and stretchability of the PEDOT:PSS films. AgNWs are interconnected, yielding a nanomesh structure. The nanomesh design enables excellent gas permeability and stretchability of the nanocomposite. Silver nanomesh (AgNM) and PEDOT:PSS nanofibrils form interpenetrating networks, offering high electrical conductivity and electromechanical stability of the nanocomposites (FIG. 1B). The stacked structure of the nanocomposite provides a soft and smooth PEDOT:PSS surface to contact the skin and yields a low electrical interface impedance due to the combined high ionic and electronic conductivity.

Figure 1C:
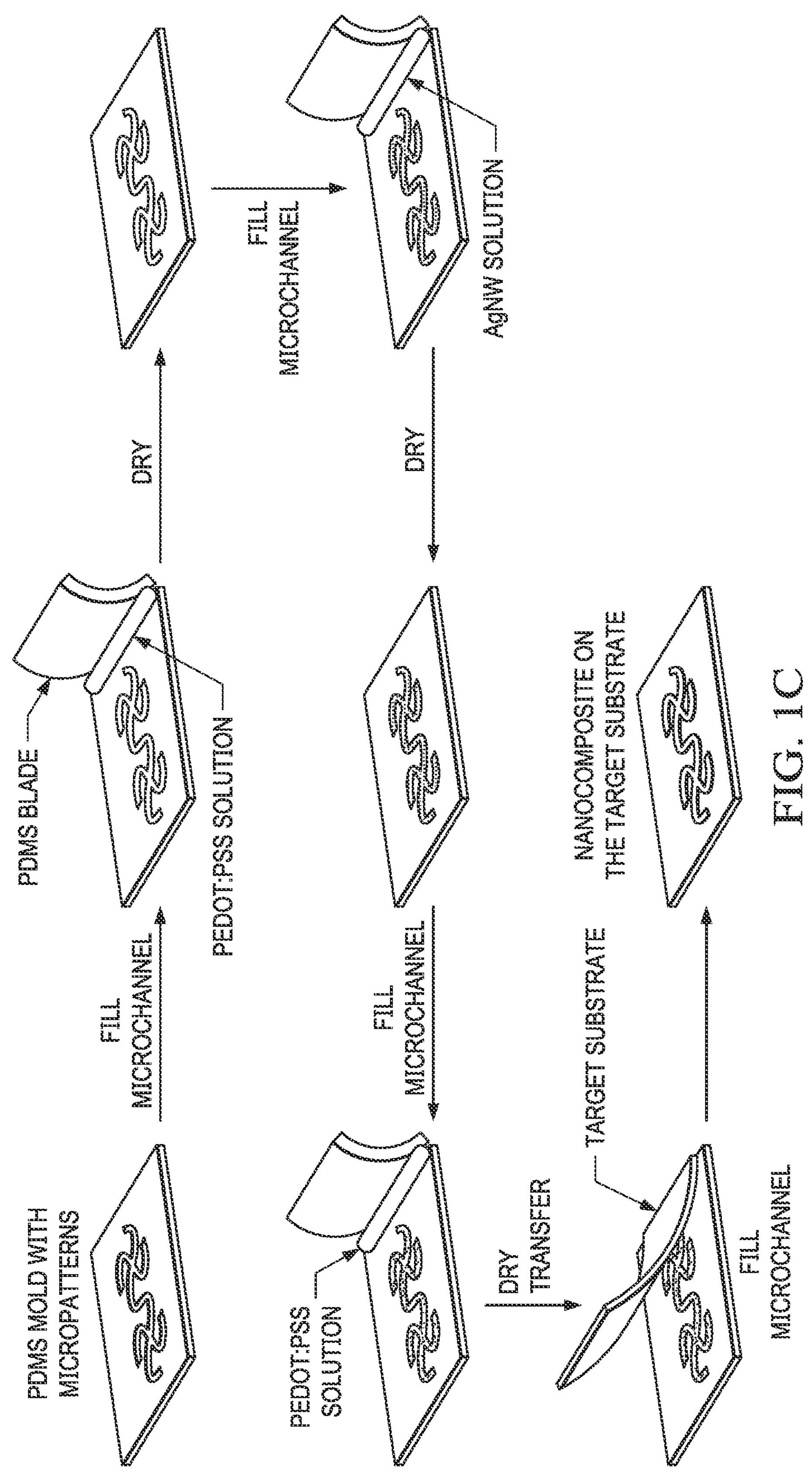
Figure 2:
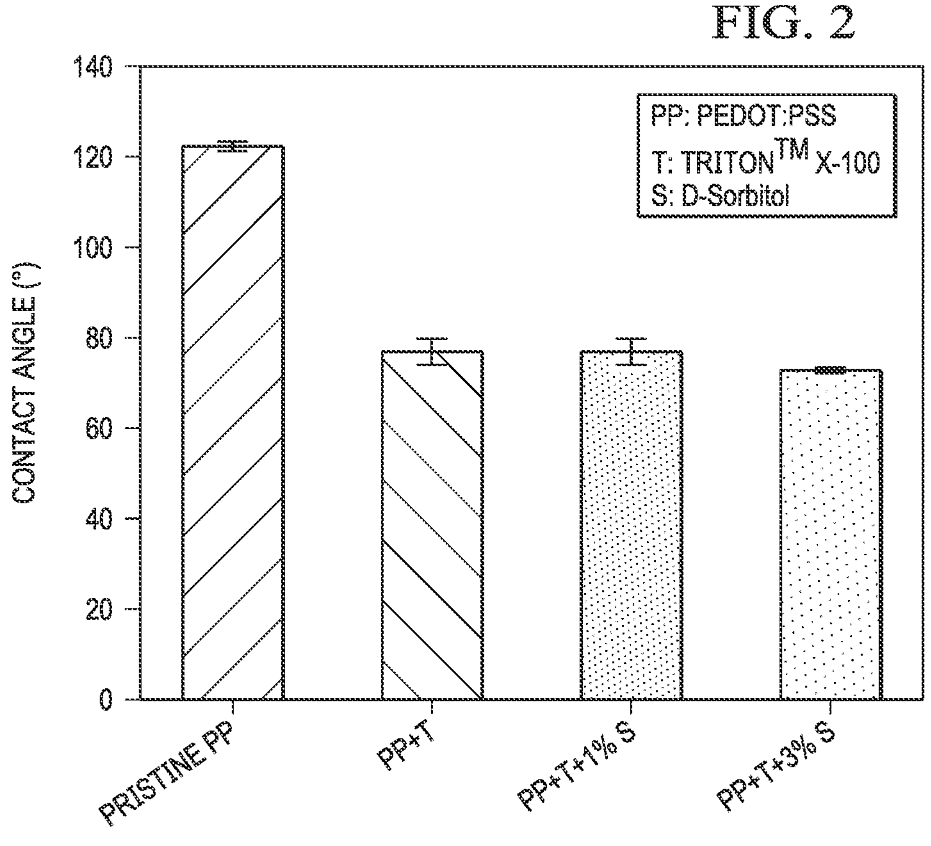
FIG. 2 illustrates corresponding contact angles for poly (3,4-ethylenedioxythiophene):poly(styrenesulfonate) (PEDOT:PSS) droplets with and without TRITON™ X-100 on a polydimethylsiloxane (PDMS) surface.

Solution-processed nanomaterials were patterned via a simple, low-cost micromolding process and then transferred print the patterned nanocomposites on various substrates to achieve nanocomposite electrophysiological sensors (FIG. 1C). Compared to previously reported micromolding in capillaries, this approach does not require the mold placed on a support to form microchannels, thereby allowing for the fabrication of nanocomposites with any desired micropatterns, including the non-interconnected patterns. This fabrication approach does not rely on standard microfabrication procedures, including vacuum deposition, spin coating, photolithography, or wet and dry etching. In addition, compared to the subtractive manufacturing process, it minimizes materials waste. The fabrication steps generally include (i) preparation of a polydimethylsiloxane (PDMS) mold with desired micropatterns, (ii) filling the microchannel with PEDOT:PSS solution with a PDMS blade, (iii) film drying at 60° C. for min, (iv) repeating the step (ii) and (iii) with AgNW solution and PEDOT:PSS solution, followed by annealing at 130° C. for 30 min, and (v) transferring the composite to a target substrate. The width of the microchannel in the PDMS mold ranges from 25 μm to 250 μm, and the depth is ~50 μm. The PDMS mold can be reused with unlimited numbers. The pristine PEDOT:PSS aqueous solution does not uniformly fill the PDMS microchannels after blading due to the poor wetting of the PEDOT:PSS solution on the hydrophobic surface. A small amount of a nonionic surfactant (TRITON™ X, 3 wt %) was added to achieve uniform filling. The addition of TRITON™ X reduces the contact angle of the PEDOT:PSS solution on the PDMS surface from 122° to 77°, confirming the improved wetting (FIG. 2). It should be noted that TRITON™ X also reduces the interfacial adhesion between the PEDOT film and the PDMS, enabling the easy transfer of the film onto various target substrates.

The nanocomposite thickness can be tuned by the concentration of the precursor solutions and the number of blading depositions. Twice depositions of each layer yield ~1.2 μm thick nanocomposite. The dimension and density of AgNWs can tune the conductivity of the nanocomposite according to percolation studies. After coating AgNWs on the PEDOT:PSS, a scanning electron microscope (SEM) image reveals the uniform distribution of AgNWs with a diameter of ~250 nm and a length of 10 μm to 20 μm and the interpenetrating interface between AgNWs and PEDOT:PSS layer. SEM images of the nanocomposite after one-time deposition of the PEDOT:PSS on AgNWs show a rough surface topography following the AgNM underneath. A tilted SEM image shows the nanocomposite surface becomes smooth after the second deposition of the PEDOT:PSS. The image also confirms the stacked structure of the nanocomposite with an AgNM sandwiched between PEDOT:PSS layers. The cross-section SEM image of the nanocomposite further confirms that the PEDOT:PSS and AgNM form an interpenetrating network to yield a mechanically stable nanocomposite. Optical microscope images of a PDMS mold filled with PEDOT:PSS, AgNW, and PEDOT:PSS were analyzed subsequently after drying. The color changes from uniform light blue to light yellow to deep blue following each deposition. Dark-field optical microscope images further confirm the uniform distribution and interconnected structure of AgNWs.

Transfer printing of nanocomposite thin films. Current low-cost methods to pattern AgNWs include screen printing and stencil printing, which yield the feature dimension mostly larger than 100 μm. The micropatterning strategy described above can produce ultrathin nanocomposites of arbitrary and complex geometries with a feature dimension less than 25 μm. Optical microscope images of nanocomposites with serpentine patterns printed on 3M™ TEGADERM™ adhesives were analyzed. The wire width of the nanocomposite filaments ranged from 150 μm to 25 μm. With this facile fabrication approach, the patterned nanocomposite can easily integrate with common adhesive substrates to yield electronic devices with different adhesion and breathability based on the user preference and applications. Images of the nanocomposite with a wire width of 150 μm over a centimeter-scale area transferred onto silicone adhesives on fabric and polyimide substrates and acrylic adhesives on fabric and water-soluble cellulose paper were reviewed. Silicone adhesives provide mild adhesion to the skin, ideal for people with sensitive skin or scarred skin. In contrast, acrylic adhesives provide strong adhesion to the skin, thereby more traumatic to the skin during removal.

Figure 3:
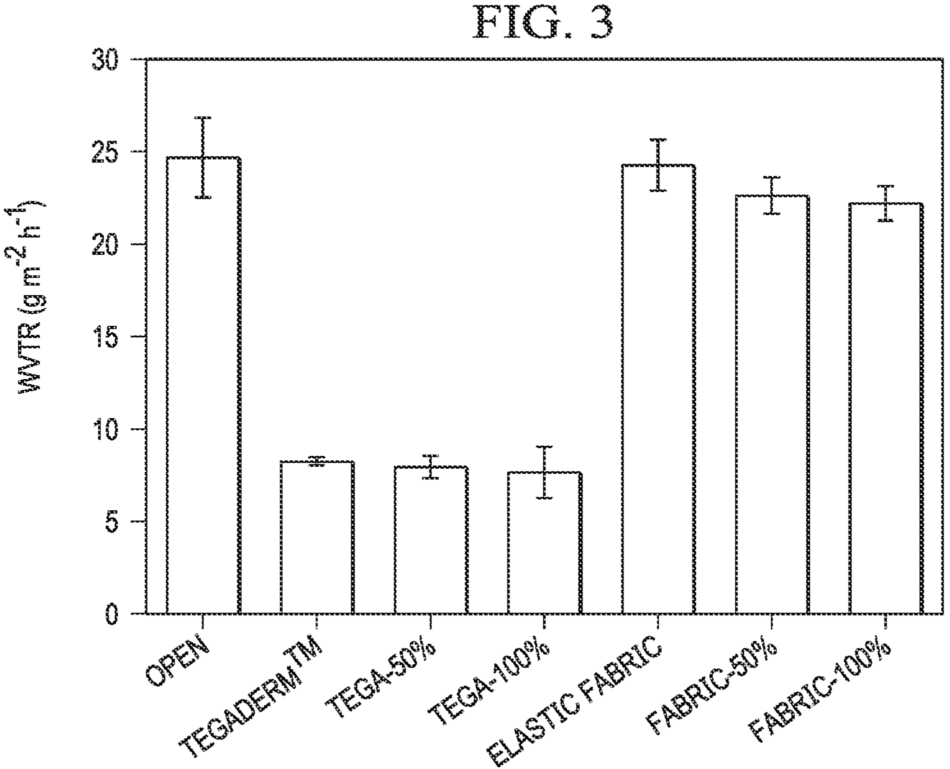
FIG. 3 illustrates water vapor transmission rate (WVTR) comparison of nanocomposite thin films on medical adhesives with different breathability and open bottle control.

Photographs of a representative nanocomposite electrode with a serpentine pattern laminated on the forearm at rest and compressed state were reviewed. The electrode followed the natural deformation of the skin without constraint or delamination, confirming its good conformability to the skin. Previously reported gas-permeable electrodes and substrates have significantly improved perspiration transport and evaporation, thereby minimizing skin irritation and inflammation risks after long-term wear. To evaluate the breathability of the nanocomposite, water vapor transmission rate (WVTR) was measured through the nanocomposite laminated on the medical-grade adhesive substrates with different breathability (FIG. 3). With different substrates, properties that range from full breathability to constrained transdermal loss can be achieved. The 3M™ TEGADERM™ shows three times lower WVTR than the value determined without any cover layer, shown as the open case in the results. The elastic nonwoven fabric medical tape (3M™ 9907W) is highly breathable with a similar WVTR as the open case. The nanocomposite with a serpentine pattern of 50% fill factor (conductive area/electrode area) and with 100% fill factor (a fully covered film) on both substrates show less than 10% decrease in WVTR than that measured from the substrates only. These results suggest that the nanocomposite has a negligible effect on the WVTR of the devices.

Electromechanical characterization of nanocomposite thin films. To validate the electromechanical stability of nanocomposite thin films, the effect of dual additives, that is, TRITON™ X and D-sorbitol, on the mechanical and electrical properties of PEDOT:PSS films was first investigated. FIG. 4A shows the stress-strain curves of PEDOT:PSS films with 3 wt % TRITON™ X and varying concentrations of D-sorbitol from 0 wt % to 3 wt %, obtained by uniaxial tensile testing. With the increase of D-sorbitol, the elongation of the PEDOT:PSS films at break increases while Young's modulus decreases. The PEDOT:PSS film without D-sorbitol exhibit an elongation of ~12% at the break, Young's modulus of ~88 MPa, and tensile strength of ~7 MPa. The addition of D-sorbitol decreases Young's modulus of the PEDOT:PSS films. The tensile strength decreases from 1.9 to 1.5 Mpa, and Young's modulus decreases from 11.1 to 8.8 Mpa, with the concentration of D-sorbitol increasing from 1 wt % to 3 wt %. The elastic modulus of the PEDOT films was also measured by microindentation tests. The stress relaxation curves characterize the viscoelastic behavior of the PEDOT:PSS films (FIG. 4B). FIG. 4C shows elastic moduli comparison of the PEDOT:PSS films calculated from FIG. 4A and FIG. 4B. The hold segments were fitted using a two-exponent exponential decay equation to determine the load at equilibrium (FIGS. 5A-5C). The calculated elastic modulus of the PEDOT:PSS films decreases from 15.0 to 1.7 Mpa with increasing the concentration of D-sorbitol from 0 to 3 wt %. The elastic modulus determined by indentation tests is 3 to 6 times lower than the tensile modulus, which likely results from the preferential alignment of PEDOT:PSS nanofibrils parallel to the film plane. The elastic moduli of the skin at different body locations and orientations range from 0.54 to 1.95 MPa. These results show that the modulus of the PEDOT:PSS film with D-sorbitol is comparable with that of the skin, which can facilitate its conformal contact with the skin.

The conductivity of the PEDOT:PSS films with 3 wt % TRITON™ X was measured to be ~93 S/cm. It increased to ~167 S/cm with the addition of 3 wt % D-sorbitol. Conductive nanocomposite films with a serpentine pattern of 50% fill factor, 150 μm wire width, and ~1.2 μm thickness were prepared using the PEDOT:PSS solution with 3 wt % TRITON™ X and 3 wt % D-sorbitol for the following measurements. The sheet resistance of ~1.2 μm thick nanocomposite serpentine film is ~70 Ω/sq, much lower than that of the PEDOT:PSS film without AgNWs (~120 Ω/sq). The electromechanical stability of the nanocomposite films was evaluated by measuring the resistance changes under bending and stretching and compared them with those of the films without AgNWs. The bending tests were performed by wrapping thin films on the cylinders with varying radius from 0.125 mm to 7 mm. The resistance of the thin films increases under bending with decreasing the bending radius (FIG. 4D). The nanocomposite films exhibit less than an 8% increase in the resistance under bending, much smaller than that of the PEDOT:PSS films. Under uniaxial stretch, the resistance of the nanocomposite films increases by 5% under 30% strain and 1.5 times under 60% strain (FIG. 4E). In contrast, the resistance of PEDOT:PSS films increases by 50% under 30% strain and 24.8 times under 60% strain, much higher than the resistance change of the nanocomposite. Cyclic stretch and release tests at 30% strain were performed to evaluate the electromechanical stability and durability of the nanocomposite film. The resistance increase of the nanocomposite is ~11% after 450 stretch and release cycles, much lower than the resistance increase ~118% of the PEDOT:PSS film (FIG. 4F).

Electrophysiological monitoring with nanocomposite sensors. Previously developed epidermal electrophysiological sensors with optimal mechanics design provide comparable signal quality to standard Ag/AgCl gel electrodes. In contrast, the nanocomposite sensors presented herein provide a lower skin-electrode interface impedance and a higher signal-to-noise ratio than the standards. Electrochemical impedance spectroscopy was used to measure the skin-electrode interface impedance as a function of frequency. The interface impedance measured with nanocomposite electrodes and standard Ag/AgCl gel electrodes was compared (FIG. 6A). The effective conductive area of nanocomposite electrodes is around 0.9 $cm^2$, approximately half of the conductive gel area of Ag/AgCl electrodes. The interface impedance decreases with increasing the frequency from 1 Hz to 10 kHz, relevant to the frequency of electrophysiological signals. The impedance with Ag/AgCl gel electrodes is 2.8 times higher at 1 Hz and 1.7 times higher at 100 Hz than those measured with nanocomposite electrodes. The lower interface impedance of the nanocomposite electrodes mainly results from the combined high ionic and electronic conductivity of the PEDOT:PSS and AgNM.

It was demonstrated that nanocomposite electrodes can provide robust ECG, EMG, and bioimpedance recordings. ECG records the electrical activity of the heart. It is a standard test for detecting numerous cardiac abnormalities, such as atrial fibrillation and myocardial infarction. EMG measures the electrical activity of skeletal muscles, which can evaluate the function of muscles and the nerve cells that control them and serve as an input signal for human-machine interaction. To compare the performance of nanocomposite and standard Ag/AgCl gel electrodes for these recordings, the electrodes were mounted onto a human subject's chest for ECG and forearm for EMG (FIG. 6B). FIG. 6C shows the ECG signals collected with nanocomposite and gel electrodes. Both waveforms reveal important features of ECG, including P wave, QRS complex, and T-wave. The nanocomposite electrodes provide ECG signals with a peak-to-peak voltage of 2.56 mV, higher than that collected with gel electrodes (2 mV). To measure EMG, a pair of electrodes were placed on the flexor muscles of the forearm to measure the muscle contract intensity induced by a fixed gripping force. FIG. 6D shows the EMG signals measured with nanocomposite electrodes and gel electrodes following three cycles of muscle contractions for 3 seconds and rest for 5 seconds. The signal and noise of EMG recordings are calculated from the rectified voltages induced by muscle contractions and at rest state, using the root-mean-squared (RMS) analysis. The RMS noise with the nanocomposite electrodes is around 10 μV, lower than that of gel electrodes (16 μV). The signal-to-noise ratio of EMG signals with nanocomposite electrodes is 12.7 dB, higher than 9.5 dB with gel electrodes. After the human subject wore the electrodes for 8 hours, the noise with the gel electrodes increased to 19 μV. In contrast, the signal quality of EMG measured with the nanocomposite electrode remains the same.

To demonstrate large-area electrophysiological sensing, an array of nanocomposite electrodes with an overall dimension of 2 cm×8 cm and individual electrodes of 1 cm×1 cm were fabricated for bioimpedance recordings on the wrist. Bioimpedance measurement is a promising approach to obtain the pulse waveform that continuously reflects the blood pressure changes through the impedance change in the local artery. Previous studies rely on rigid electrodes to measure bioimpedance and show that the electrode-skin impedance with rigid electrodes is much higher than that with gel electrodes. The nanocomposite electrodes reported herein provide lower interface impedance and higher signal quality than gel electrodes. An electrode array laminated on the wrist along the radial artery for bioimpedance measurements with a four-probe configuration was utilized. Two outer electrodes inject a small alternating current of 400 μA at 100 kHz while two inner electrodes measure the voltage change over time. FIG. 7A shows bioimpedance recording over four pulse periods measured with nanocomposite electrodes. The derivative of the impedance magnitude dZ/dt was calculated and shown with positive polarity (FIG. 7B). A characteristic pulse waveform exhibits three distinguishable peaks, including the Percussion wave (P wave), the Tidal wave (T wave), and the Dicrotic wave (D wave). These peaks result from the ejection of blood from the left ventricle into the aorta, reflected waves from the hand and the lower body, and the aortic valve closure. The bioimpedance waveform measured with nanocomposite sensors clearly exhibits these three peaks. The radial augmentation index $AI_r$ (amplitude of P wave/amplitude of T wave) can diagnose arterial stiffness. In the measurements presented herein, the $AI_r$ is calculated to be ~49%, consistent with the value reported for a healthy adult male of 25 years old. In contrast, gel electrodes show a higher impedance magnitude than nanocomposite electrodes (FIG. 7C). The T wave is not clearly distinguishable in the bioimpedance waveform collected with the gel electrodes. In addition, the dZ/dt derived from the nanocomposite sensors is 1.7 times larger than the gel system (FIG. 7B and FIG. 7D). These results collectively confirm the higher quality of electrophysiological signals measured using nanocomposite sensors, compared to standard gel electrodes.

In summary, moldable and transferrable conductive nanocomposites that leverage synergistic properties of AgNWs and PEDOT:PSS for soft and stretchable skin-interfaced electronic devices have introduced. A simple, low-cost micromolding approach can pattern solution-processed nanocomposites with a feature dimension less than 25 μm. The patterned nanocomposite thin films can be transferred onto various substrates to realize electronic devices with high breathability. The nanocomposite films exhibit excellent electromechanical stability validated by bending and stretching measurements. The electrophysiological signals collected with the nanocomposite sensors exhibit a higher signal-to-noise ratio than those with standard gel sensors. The nanocomposite design and fabrication strategy introduced here can be broadly employed for realizing various soft and stretchable devices, such as wearable sensors and actuators.

Reference will now be made to particular materials and methods utilized by various embodiments of the present disclosure. However, it should be noted that the materials and methods presented below is for illustrative purposes only and is not intended to limit the scope of the claimed subject matter in any way.

Materials. Poly(3,4-ethylenedioxythiophene):poly(styrenesulfonate) was purchased from Ossila Ltd. TRITON™ X-100, ethyl glycol, silver nitrate, polyvinylpyrrolidone (PVP, Mw=59,000), copper chloride, D-sorbitol, and 1H,1H,2H,2H-perfluorooctyltrichlorosilane (FDTS) were purchased from Fisher Scientific. Polydimethylsiloxane (PDMS, SYLGARD™ 184) was obtained from Dow Corning. SU-8 and its developer were obtained from Kayaku Advanced Materials, Inc. All chemicals were used as purchased.

Synthesis of silver nanowire. AgNWs with a diameter of ~250 nm and a length of 10 μm to 20 μm were synthesized using a previously reported polyol method with slight modifications. PVP (0.3 M, 10 mL), silver nitrate (0.3 M, 2 mL), and copper chloride (0.015 M, 0.02 mL) solutions were prepared using ethyl glycol (EG) as a solvent. The PVP solution was heated at 170° C. for 0.5 hours. Subsequently, copper chloride and silver nitrate solutions were added under stirring and left for 50 minutes for silver nanowires to grow. The AgNW solution was then quenched in an ice-cold bath and centrifuged at 8000 RPM for 30 minutes to remove the supernatant and dispersed in ethanol for future usage.

Preparation of PDMS molds. SU-8 masters were fabricated on 4-inch silicon wafers using photolithography. First, a silicon wafer is cleaned and coated with SU-8 2050 to achieve a thickness of ~50 μm. The coated wafer was then heated at 65° C. for 3 minutes and 95° C. for 9 minutes on a hot plate. Once the wafer cooled down, it was exposed to UV energy of 200 $mJ/cm^2$ and heated similarly to the pre-bake protocol. The SU-8 photoresist was developed using a SU-8 developer with 4 minutes of agitation. The wafer was finally rinsed with isopropyl alcohol (IPA). Next, the SU-8 master was treated with FDTS vapor in a vacuum container for 30 minutes to reduce the adhesive between SU-8 and PDMS. PDMS was poured onto the wafer and placed under a vacuum for an hour to remove any air bubbles. Lastly, PDMS was cured at 60° C. for two hours in an oven and then removed from the SU-8 master.

Fabrication of electrodes. A conductive nanocomposite electrode composed of three layers, includes top and bottom PEDOT:PSS and middle AgNW layers. Following steps described in FIG. 1C, PEDOT:PSS and AgNW solutions sequentially filled the channel in a PDMS mold, followed by removing access solution with a PDMS blade and drying at 60° C. for five minutes to remove solvents. The PEDOT:PSS solution was blended with TRITON™ X (3 wt %) and a varying amount of D-sorbitol (0 wt % to 3 wt %). The nanocomposite thickness is around 1.2 μm, with each layer obtained by blading twice. Once the coating of all the layers was complete, the electrodes were annealed at 130° C. for 30 minutes. The electrodes were transferred onto adhesives after pressing the adhesive laminated on the PDMS mold with a tweezer and peeling off the adhesive from the mold. The transferred electrodes can be cut into different dimensions for further measurements. Finally, anisotropic conductive films were used to connect the electrodes to data acquisition systems.

Materials Characterization. SEM images were recorded on an ultrahigh-resolution field emission scanning electron microscope (JEOL JSM-7500F). The tensile stretch and cyclic stretch and release measurements were conducted using MARK-10. The strain was applied at the rate of 5 mm/min in tensile measurements. In microindentation tests, the elastic modulus was calculated using the Hertzian equation:

$$E = \frac{3}{4\sqrt{R}} \frac{1 - v^2}{h^{3/2}} \gamma_o,$$

where $\gamma_0$ represents the load at equilibrium, E is the effective elastic modulus, R is the spherical probe's radius, h is the displacement, and v is the Poisson's ratio of the sample. The thin film resistance was recorded with a digital multimeter (NI-USB4065) using a four-probe method. The skin-electrode impedance was measured with a potentiostat (Gamry).

Electrophysiological measurements. ECG and EMG were measured using BIOPAC (MP160, ECG 100D, and EMG 100D). Three electrodes, including an anode, cathode, and ground electrodes, were attached around the heart for ECG measurements. Bipolar EMG signals were collected with two electrodes on the forearms and one ground electrode on the elbow to measure the intensity of brachioradialis muscle contraction. Bioimpedance signals were obtained using BIOPAC (MP160 and NICO100C). Four electrodes were placed along the radial artery close to the wrist on the forearm. The two outer electrodes inject a small current of 400 μA, while the two inner electrodes measure the voltage and convert it to the impedance. A 10 Hz low pass filter and direct current (DC) high pass filter were applied in the bioimpedance measurements.

As some sensor applications require various number of layers of the electrodes presented herein, in various aspects, the electrode can have one, two, or three layers. For example, for some applications where only one layer is required by a sensor, the electrodes of the present disclosure can include a single layer with a conductive polymer, or a single layer with an inorganic material. Additionally, some applications may dictate that the sensor only requires two layers. As such, the electrodes of the present disclosure can also include a first layer that includes a conductive polymer and a second layer that includes an inorganic material that forms a conductive layer on the first layer. As an additional example, some applications may require three layers on the electrode. In such applications, the electrodes of the present disclosure can include a first layer having a conductive polymer, a second layer having an inorganic material that forms a conductive network on the first layer, and a third layer having an additional conductive polymer.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. An electrode comprising:

a first layer comprising a conductive polymer;

a second layer positioned above the first layer and comprising an inorganic material that forms a conductive network on the first layer, wherein the inorganic material is in a form selected from the group consisting of patterns, arrays, nanoparticles, nanofibers, nanowires, nanomeshes, and combinations thereof; and a third layer positioned above the second layer and comprising a conductive polymer selected from the group consisting of (3,4-ethylenedioxythiophene) (PEDOT), poly(3,4-ethylenedioxythiophene):poly(stryrenesulfonate) (PEDOT:PSS), poly(pyrrole)s (PPY), polyanilines (PANI), and combinations thereof, wherein the conductive polymer of the first layer is in a form of nanofibrils.

2. The electrode of claim 1, wherein the electrode is encapsulated with an adhesive.

3. The electrode of claim 1, wherein the conductive polymer of the first layer is an intrinsically conducting polymer selected from group consisting of poly(3,4-ethylenedioxythiophene) (PEDOT), poly(3,4-ethylenedioxythiophene): poly(styrenesulfonate) (PEDOT: PSS), poly(pyrrole)s (PPY), polyanilines (PANI), and combinations thereof.

4. The electrode of claim 1, wherein the conductive polymer of the first layer; further comprises a dopant.

5. The electrode of claim 4, wherein the dopant is selected from the group consisting of 2-[4-(2,4,4-trimethylpentan-2-yl) phenoxy] ethanol, D-sorbitol, dimethyl sulfoxide, ionic liquids, and combinations thereof.

6. The electrode of claim 1, wherein the inorganic material is selected from the group consisting of platinum, gold, silver, copper, silver chloride and combinations thereof.

7. The electrode of claim 1, wherein the inorganic material is in the form of at least one of silver nanowire (AgNW) or silver nanomesh (AgNM).

8. The electrode of claim 1, wherein the electrode is in a form of a composite.

9. The electrode of claim 1, wherein the third layer encapsulates the inorganic component.

10. The electrode of claim 1, wherein the third layer coats the inorganic component.

11. The electrode of claim 1, wherein the electrode is at least one of wearable or implantable.

* * * * *